United States Patent
You et al.

(10) Patent No.: US 9,039,628 B2
(45) Date of Patent: May 26, 2015

(54) TOUCH-SENSITIVE DISPLAY APPARATUS CAPABLE OF MEASURING PULSE RATE AND METHOD THEREOF

(75) Inventors: Qiang You, Shenzhen (CN); Yin-Zhan Wang, Shenzhen (CN); Tsung-Jen Chuang, New Taipei (TW); Shih-Fang Wong, New Taipei (TW)

(73) Assignees: Fu Tai Hua Industry (Shenzhen) Co., Ltd., Shenzhen (CN); HON HAI PRECISION INDUSTRY CO., LTD., New Taipei (TW)

( * ) Notice: Subject to any disclaimer, the term of this patent is extended or adjusted under 35 U.S.C. 154(b) by 531 days.

(21) Appl. No.: 13/205,625

(22) Filed: Aug. 9, 2011

(65) Prior Publication Data

US 2012/0226175 A1    Sep. 6, 2012

(30) Foreign Application Priority Data

Mar. 4, 2011   (TW) .................. 201110052816.5

(51) Int. Cl.
    *A61B 5/024*   (2006.01)

(52) U.S. Cl.
    CPC ....................... *A61B 5/024* (2013.01)

(58) Field of Classification Search
    CPC ........ A61B 5/024; A61B 5/0255; A61B 5/02; A61B 5/02438; A61B 5/02444; A61B 5/11; G06F 2203/04104; G06F 1/1643; G06F 3/04; H04M 2250/22
    USPC .................................................. 600/500–503
    See application file for complete search history.

(56) References Cited

U.S. PATENT DOCUMENTS

| | | | | |
|---|---|---|---|---|
| 4,195,642 A | * | 4/1980 | Price et al. ................. | 600/502 |
| 4,248,244 A | * | 2/1981 | Charnitski et al. ........... | 600/519 |
| 6,549,756 B1 | * | 4/2003 | Engstrom .................. | 455/66.1 |
| 7,269,458 B2 | * | 9/2007 | Kadhiresan et al. ........... | 607/19 |
| 8,320,985 B2 | * | 11/2012 | Miller ........................ | 600/324 |
| 8,615,290 B2 | * | 12/2013 | Lin et al. .................... | 600/509 |
| 2008/0113650 A1 | * | 5/2008 | Engstrom .................. | 455/411 |
| 2009/0084612 A1 | * | 4/2009 | Mattice et al. ............. | 178/18.04 |
| 2009/0216132 A1 | * | 8/2009 | Orbach ..................... | 600/485 |
| 2010/0113950 A1 | * | 5/2010 | Lin et al. .................... | 600/509 |
| 2010/0256470 A1 | * | 10/2010 | Miller ........................ | 600/324 |

* cited by examiner

*Primary Examiner* — Navin Natnithithadha
*Assistant Examiner* — Meredith Weare
(74) *Attorney, Agent, or Firm* — Novak Druce Connolly Bove + Quigg LLP

(57) ABSTRACT

A touch-sensitive display apparatus includes a multi-touch screen, a processor, and a network unit. The processor controls the apparatus to enter a pulse rate measuring mode, records the number of the touched touch points in each scanning period, and determines a curve according to all the recorded numbers within a preset period, the number of wave crests of the curve, and pulse rates per minute according to the number of the wave crests. A related method is also provided.

8 Claims, 3 Drawing Sheets

TOUCH-SENSITIVE DISPLAY APPARATUS CAPABLE OF MEASURING PULSE RATE AND METHOD THEREOF

BACKGROUND

1. Technical Field

The present disclosure relates to touch-sensitive display apparatus, and particularly, to a touch sensitive display apparatus with a pulse rate measuring function and a method thereof.

2. Description of Related Art

Although various pulse rate measuring instruments, either for human beings or animals, can satisfy the basic requirements, a new pulse rate measuring instrument is still desirable.

BRIEF DESCRIPTION OF THE DRAWINGS

The components of the drawings are not necessarily drawn to scale, the emphasis instead being placed upon clearly illustrating the principles of a touch-sensitive display apparatus and a method thereof. Moreover, in the drawings, like reference numerals designate corresponding parts throughout several views.

DETAILED DESCRIPTION

Figure 1:
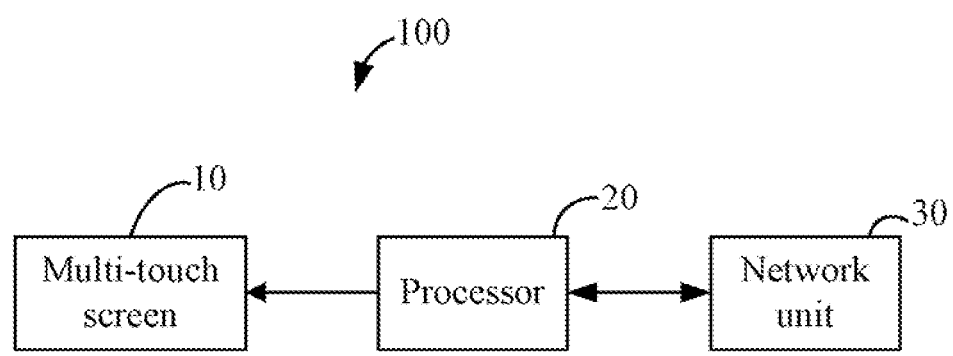
FIG. 1 is a block diagram of a touch-sensitive display apparatus in accordance with an exemplary embodiment.

Referring to FIG. 1, a touch-sensitive display apparatus 100 includes a multi-touch screen 10, a processor 20, and a network unit 30. The multi-touch screen 10 may be a capacitive touch screen.

Figure 2:
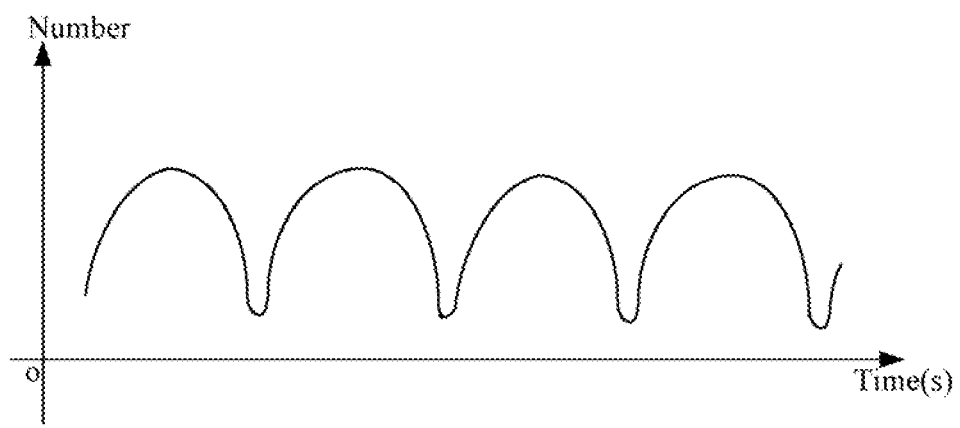
FIG. 2 is a schematic view of a curve obtained according to the number of touched touch points in each scanning period.

The processor 20 controls the apparatus 100 to enter a pulse rate measuring mode in response to a user input. When entering the pulse rate measuring mode, the apparatus 100 can be used to measure pulse rates per minute of a user. When inner side of a wrist (the portion of the wrist where the pulse can be measured) of the user is placed on the screen 10, a number of touch points of the screen 10 are touched. When the artery throbs once, the skin of the wrist around the artery gradually expands, thus the number of the touched touch points gradually increases. Before the artery throbs once again, the skin of the wrist around the artery gradually shrinks, thus the number of the touched touch points gradually decreases. The processor 20 records the number of the touched touch points in each scanning period. The processor 20 further determines a curve according to all the recorded numbers of the touched touch points within a preset period (see FIG. 2), the number of wave crests of the curve, and pulse rates per minute according to the number of the wave crests. In this embodiment, each scanning period is far less than the preset period. The preset period may be one minute or more than one minute. The number of the artery throbbing within the preset period is the number of the wave crests minus one, and the number of the artery throbbing within the preset period divided by the preset period is the pulse rates per minute. The processor 20 further displays the determined pulse rates per minute on the screen 10.

The processor 20 further generates a prompt to indicate that the determined pulse rates per minute may be abnormal when determining that the determined pulse rates per minute is not within a preset range. Each pulse rates per minute within the preset range may be the normal pulse rates per minute for adults.

The network unit 30 communicates the apparatus 100 with a network, for example, the Internet. When the processor 20 determines that the determined pulse rates per minute is not within the preset range, the processor 20 transmits the determined pulse rates per minute to a designated medical webpage through the network unit 30 to obtain medical help information from the designated webpage.

Figure 3:
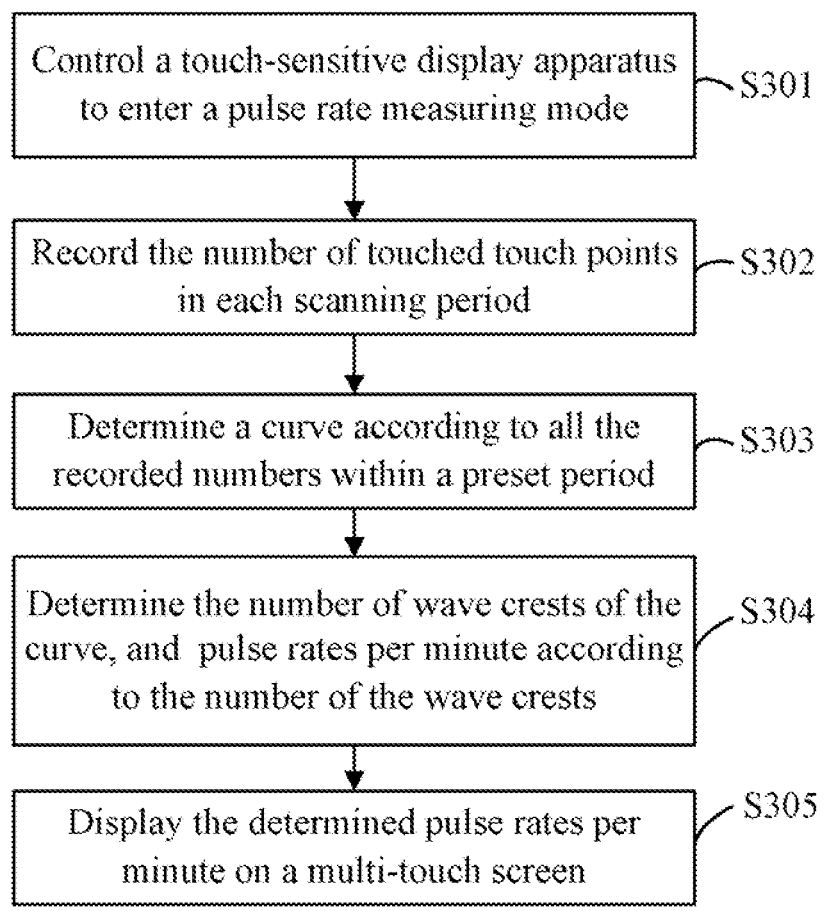
FIG. 3 is a flowchart of a pulse rate measuring method in accordance with an exemplary embodiment.

FIG. 3 is a flowchart of a pulse rate measuring method in accordance with an exemplary embodiment.

In step S301, the processor 20 controls the apparatus 100 to enter the pulse rate measuring mode in response to a user input.

In step S302, the processor 20 records the number of the touched touch points in each scanning period.

In step S303, the processor 20 determines a curve according to all the recorded numbers of the touched touch points within the preset period.

In step S304, the processor 20 determines the number of wave crests of the curve, and pulse rates per minute according to the number of the wave crests. In this embodiment, each scanning period is far less than the preset period. The preset period may be one minute or more than one minute. The number of the artery throbbing within the preset period is the number of the wave crests minus one, and the number of the artery throbbing within the preset period divided by the preset period is the pulse rates per minute.

In step S305, the processor 20 displays the determined pulse rates per minute on the screen 10.

In this embodiment, when determining that the determined pulse rates per minute is not within the preset range, the processor 20 further generates a prompt to indicate that the determined pulse rates per minute may be abnormal, and transmits the determined pulse rates per minute to a designated medical webpage through the network unit 30 to obtain medical help information from the designated webpage.

Although the present disclosure has been specifically described on the basis of the exemplary embodiment thereof, the disclosure is not to be construed as being limited thereto. Various changes or modifications may be made to the embodiment without departing from the scope and spirit of the disclosure.

What is claimed is:

1. A touch-sensitive display apparatus comprising:
   a multi-touch screen configured to detect physical contact therewith; and
   a processor configured to:
   control the touch-sensitive display apparatus to enter a pulse rate measuring mode;
   for a plurality of scanning periods, detect a quantity of touch points on the multi-touch screen during sustained continuous contact by a user in each scanning period when in the pulse rate measuring mode;
   receive the quantity of the touch points from the multi-touch screen and generate a curve according to the recorded quantity of the touch points in each scanning period within a preset period;
   detect a quantity of wave crests of the curve;
   determine pulse rate per minute according to the quantity of the wave crests, wherein the processor is configured to determine pulse rate per minute by determining that a quantity of an artery throbbing within the preset period is the quantity of the wave crests minus one, and determining pulse rate per minute as the quantity of the artery throbbing within the preset period divided by the preset period; and output the determined pulse rate per minute to the multi-touch screen for displaying the determined pulse rate per minute on the multi-touch screen.

2. The touch-sensitive display apparatus as described in claim 1, wherein the preset period is one minute or more than one minute.

3. The touch-sensitive display apparatus as described in claim 1, wherein the processor is further configured to generate a prompt to indicate that the determined pulse rate per minute is abnormal when the processor is determining that the determined pulse rate per minute is not within a preset range.

4. The touch-sensitive display apparatus as described in 1, further comprising a network unit to communicate the touch-sensitive display apparatus with a network, wherein the processor is further configured to transmit the determined pulse rate per minute to a designated medical webpage through the network unit to obtain medical help information from the designated webpage when the processor is determining that the determined pulse rate per minute is not within a preset range.

5. A pulse rate measuring method applied in a touch-sensitive display apparatus, the touch-sensitive display apparatus comprising a multi-touch screen configured to detect physical contact therewith, the method comprising:

receiving, from a processor, a command at the touch-sensitive display apparatus to enter a pulse rate measuring mode;

detecting a quantity of touch points on the multi-touch screen during sustained continuous contact by a user, wherein the detecting of the quantity of the touch points occurs during a plurality of scanning periods that are each controlled by the processor;

transmitting data, corresponding to each of the plurality of scanning periods, of the quantity of the touch points to the processor;

generating, by the processor, a curve from the data of the quantity of the touch points for each scanning period;

determining a quantity of wave crests of the curve by the processor;

determining pulse rate per minute according to the quantity of the wave crests by the processor, wherein determining pulse rate per minute comprises determining a quantity of an artery throbbing within the preset period as the quantity of the wave crests minus one, and determining pulse rate per minute as the quantity of the artery throbbing within the preset period divided by the preset period; and outputting data, from the processor, to the multi-touch screen for displaying the determined pulse rate per minute on the multi-touch screen.

6. The pulse rate measuring method as described in claim 5, wherein the preset period is one minute or more than one minute.

7. The pulse rate measuring method as described in claim 5, further comprising:

generating a prompt to indicate that the determined pulse rate per minute is abnormal by the processor when the processor is determining that the determined pulse rate per minute is not within a preset range.

8. The pulse rate measuring method as described in claim 5, further comprising:

transmitting the determined pulse rate per minute to a designated medical webpage to obtain medical help information from the designated webpage by the processor when the processor is determining that the determined pulse rate per minute is not within a preset range.

\* \* \* \* \*